US010427994B2

(12) United States Patent
Thirasak et al.

(10) Patent No.: US 10,427,994 B2
(45) Date of Patent: Oct. 1, 2019

(54) SEPARATION PROCESS FOR C8 AROMATICS MIXTURE

(71) Applicants: SCG CHEMICALS COMPANY LIMITED, Bangkok Metropolis (TH); GTC Technology US, LLC, Houston, TX (US)

(72) Inventors: Attapong Thirasak, Bangkok Methropolis (TH); Alisa Kammafoo, Bangkok Methropolis (TH); Wiroon Tanthapanichakoon, Bangkok Methropolis (TH); Zhongyi Ding, Katy, TX (US); Sachin Joshi, Katy, TX (US); Arnat Prombunglum, Bangkok Methropolis (TH); Worawut Tamthaisong, Bangkok Methropolis (TH); Purachet Pitipuech, Bangkok Methropolis (TH)

(73) Assignees: SCG CHEMICALS CO., LTD., Bangkok (TH); GTC TECHNOLOGY US, LLC, Houston, TX (US)

( * ) Notice: Subject to any disclaimer, the term of this patent is extended or adjusted under 35 U.S.C. 154(b) by 63 days.

(21) Appl. No.: 15/505,593

(22) PCT Filed: Sep. 5, 2014

(86) PCT No.: PCT/US2014/054388
§ 371 (c)(1),
(2) Date: Feb. 21, 2017

(87) PCT Pub. No.: WO2016/036388
PCT Pub. Date: Mar. 10, 2016

(65) Prior Publication Data
US 2017/0240489 A1 Aug. 24, 2017

(51) Int. Cl.
*C07C 7/08* (2006.01)
*C07C 7/06* (2006.01)
*B01D 3/36* (2006.01)
*B01D 3/38* (2006.01)
*B01D 3/40* (2006.01)

(52) U.S. Cl.
CPC .................. *C07C 7/08* (2013.01); *B01D 3/36* (2013.01); *B01D 3/38* (2013.01); *B01D 3/40* (2013.01); *C07C 7/06* (2013.01)

(58) Field of Classification Search
CPC ........................ B01D 3/36–40; C07C 7/05–08
See application file for complete search history.

(56) References Cited

U.S. PATENT DOCUMENTS

| 2,532,031 | A | 11/1950 | Nixon et al. |
| 3,105,017 | A | 9/1963 | Amir et al. |
| 3,591,490 | A * | 7/1971 | Muller et al. ............ C07C 7/08 208/313 |
| 3,684,665 | A | 8/1972 | Abe et al. |
| 3,917,734 | A | 11/1975 | Derosset |
| 4,299,668 | A | 11/1981 | Berg |
| 5,135,620 | A | 8/1992 | Brown |
| 5,425,855 | A | 6/1995 | Berg |

FOREIGN PATENT DOCUMENTS

| CN | 1225081 A | 8/1999 |
| GB | 1198592 A | 7/1970 |
| JP | H11509868 A | 8/1999 |
| SU | 1097191 A3 | 6/1984 |
| WO | 2016036388 A1 | 3/2016 |

OTHER PUBLICATIONS

International Search Report and Written Opinion of the International Searching Authority for International Patent Application No. PCT/US2014/054388, dated Apr. 30, 2015 (8 pages).
First Office Action for Russian Application No. 2017111206, dated May 16, 2018, with English translation (11 pages).
Office Action for Japanese Patent Application No. 2017-533156, dated Apr. 24, 2018, with English translation (7 pages).
First Office Action for Chinese Patent Application No. 2014800816179, dated Jun. 20, 2019, with English Translation (16 pages).
He, Zicheng (2007). Principles of Chemical Engineering. China Medical Science Press. Pages 294-295 (with English translation).

* cited by examiner

*Primary Examiner* — Renee Robinson
(74) *Attorney, Agent, or Firm* — Dorsey & Whitney LLP

(57) ABSTRACT

Process for the distillative separation of ethylbenzene from a mixture comprising ethylbenzene and at least one other C8 aromatic compound, comprising distilling said mixture in a distillation column in the presence of an extractive solvent, characterized in that the distillation column is operated at a sub-atmospheric pressure.

15 Claims, No Drawings

SEPARATION PROCESS FOR C8 AROMATICS MIXTURE

TECHNICAL FIELD

The present invention relates to a process for separation of ethylbenzene from a mixture comprising ethylbenzene and at least one other C8 aromatic compound by extractive distillation.

BACKGROUND

Ethylbenzene is a hydrocarbon compound with high commercial utilization and value. It is majorly used to produce styrene which is an intermediate for polystyrene production. Ethylbenzene is commercially produced from alkylation of benzene with ethylene. However, the cost and competitive demands of ethylene and benzene prompted new efforts to recover ethylbenzene from various C8 aromatic feed streams which already contain ethylbenzene. Such feed streams are generally produced as a byproduct stream from several petrochemical processes and they usually contain ethylbenzene and one or more hydrocarbon compound with boiling point close to boiling point of ethylbenzene, especially C8 aromatic isomers.

Methods for separating ethylbenzene from other close boiling C8 aromatic compounds, especially xylene isomers, are known.

For example, U.S. Pat. No. 3,917,734 discloses an adsorptive separation process for separating ethylbenzene from a feed mixture comprising ethylbenzene and at least one xylene isomer, which process comprises contacting the feed mixture with a crystalline aluminosilicate adsorbent to selectively adsorb xylene isomers with substantial exclusion of the ethylbenzene and thereafter recovering purified ethylbenzene as a product. The separation efficiency of this process is largely relying on adsorption capacity of the adsorbent and therefore a complexed operation of countercurrent moving-bed system is preferred. Also, impurities content in the feed stream needs to be carefully controlled to prevent interference with the selective adsorption process.

Ethylbenzene can, of course, be separated from xylene isomers by fractionation but because there boiling points are very close to each other the fractionation can be achieved only with the more intricate and energy intensive system.

GB 1,198,592 discloses a process for separating C8 aromatic isomers using a single polyfunctional distillation column. The distillation is carried out in a multiplate column having at least 250 and preferably 365 trays and a reflux ratio from 100 to 250:1 in order to achieve commercially acceptable purity of ethylbenzene.

Extractive distillation is the method of separating close boiling compounds from each other by carrying out the distillation in the presence of an added solvent or so called an extractive agent. The presence of the said extractive agent in the distillation system alters the relative volatility and therefore makes possible a greater degree of separation of the close boiling compounds.

U.S. Pat. No. 3,105,017 discloses a process for separating ethylbenzene from xylene isomers by extractive distillation in the presence of a compound containing a single benzene ring substituted on the ring in at least two positions with a chloro group under condition to separate a fraction enriched in ethylbenzene.

SUMMARY OF THE INVENTION

The present invention involves an alternative and improved process for production of ethylbenzene by recovering it from a stream of hydrocarbon mixture. The process comprises distilling a mixture comprising ethylbenzene and a C8 aromatic compound in a distillation column in the presence of an extractive solvent and operating at a subatmospheric pressure.

DETAILED DESCRIPTION

The present invention relates to an extractive distillation process for ethylbenzene separation comprising distilling a mixture comprising ethylbenzene and a C8 aromatic compound in a distillation column in the presence of an extractive solvent and operating at a subatmospheric pressure.

Ethylbenzene is usually contained in a hydrocarbon stream which comprise mainly of C8 hydrocarbon compounds. The process according to the present invention is capable of effectively separating ethylbenzene from its close boiling compounds, especially C8 aromatic compounds. In an embodiment of the invention, the at least one other C8 aromatic compound comprises a compound selected from p-xylene, m-xylene, o-xylene and a mixture thereof. The mixture may further contain other components, especially in the range of C5 to C10 hydrocarbons, both aromatic and non-aromatic types. For example, the mixture may contain small amounts of benzene, toluene, styrene, and C5 to C10 paraffins, olefins, or naphthenes. The sum of these other components in the mixture is preferably less than 20 wt %, more preferably less than 15 wt %, even more preferably less than 10 wt %, and most preferably less than 5 wt %.

A solvent capable of being used as an extractive solvent must be able to alter relative volatility of components in the system of interest. Moreover, it should have a proper boiling point difference from components in the feed stream in order for it to be conveniently recovered and recycled. The extractive solvent suitable for the present invention has a boiling point above 150° C., preferably 151-290° C. Many organic compounds are qualified as an extractive solvent for the present invention. In one embodiment, the extractive solvent comprises an organic compound selected from Cl-containing compounds, S-containing compounds, N-containing compounds, O-containing compounds, and a mixture thereof.

The Cl-containing compound can be selected from 2,4-dichlorobenzene, 1,2,4-trichlorobenzene, 1,2,4,5-tetrachlorobenzene, polychlorobenzenes, benzene hexachloride, 2,3,4,6-tetrachlorophenol, 1,2,3-trichloropropane and mixtures thereof, preferably 1,2,3-trichlorobenzene and 1,2,4-trichlorobenzene.

The S-containing compound can be selected from dimethylsulfoxide, sulfolane, methyl sulfolane and mixtures thereof.

The N-containing compound can be selected from N-formylmorpholine, aniline, 2-pyrolidinone, quinolone, N-methyl-2-pyrrolidone, N-methylaniline, benzonitrile, nitrobenzene and mixtures thereof.

The O-containing compound can be selected from methyl salicylate, methylbenzoate, N-methyl-2-pyrroidone, 1,2-propanediol, 1,2-butanediol, 1,3-butanediol, benzaldehyde, phenol, tetrahydrofurfuryl alcohol, diethyl maleate, ethyl acetoacetate, 4-methoxy acetophenone, isophorone, 5-methyl-2-hexanone, 2-heptanone, cyclohexanone, 2-octanone, 2-nonanone, 3-heptanone, diisobutyl ketone, 5-nonanone, benzyl alcohol and mixtures thereof.

It is preferably that the extractive solvent comprises a Cl-containing compound. More preferably, the extractive solvent comprises a Cl-containing compound selected from 1,2,3-trichlorobenzene and 1,2,4-trichlorobenzene, most preferably 1,2,4-trichlorobenzene.

It was surprisingly found that reducing an operating pressure of the distillation column according to the present invention to sub-atmospheric level can significantly improve efficiency for separation of ethylbenzene. In particular, it has been surprisingly found that operating the distillation column at sub-atmospheric pressure achieves a high separation efficiency of ethylbenzene from a mixture comprising ethylbenzene and at least one other C8 aromatic compound. However, too low vacuum pressure can cause extremely high vapor flowrate and hence reduce the packing or tray efficiency of the column. In an embodiment, the sub-atmospheric pressure is in the range of 10 to 900 mbar, preferably 50 to 500 mbar, more preferably 100 to 300 mbar.

The distillation column operates at distributed temperature from the top to the bottom of the column which allows the more volatile fraction, in this case the ethylbenzene, to be distilled up and the less volatile fraction to be distilled down the column and results in the desired separation. In a preferred embodiment, the distillation column is operated at temperature in the range of 50 to 250° C., preferably 60 to 200° C., still more preferably 70 to 180° C.

The mass ratio of the extractive solvent to the mixture comprising ethylbenzene and the at least one other C8 aromatic compound in the distillation column is preferably in the range of 1:1 to 10:1, preferably 2:1 to 8:1, and most preferably 3:1 to 7:1.

Preferably, the process of the present invention can be operated in a hydrated environment. To create a hydrated environment, water and/or steam can be added to the distillation column, preferably in an amount of 0.1 to 25 wt % based on mass flow of the extractive solvent used.

In certain embodiments, an extra solvent may be employed, by introduction into the distillation column, to further modify relative volatility of ethylbenzene and its close boiling component to be separated. The extra solvent can be selected from Cl-containing, S-containing, N-containing, and O-containing compounds or mixtures thereof. Preferably, the extra solvent is selected from the group consisting of chloroform, carbon tetrachloride, dimethylamine, diethylamine, acetonitrile, acetaldehyde, 1-propanal, methyl isopropyl ketone, 3-methyl-2-pentanone, 3,3-dimethyl-2-butanone, 2-pentanone, 2-methylpropanal, 1-butanal, cyclopentanone, acetone, ethanol, and mixtures thereof. Usually, the extra solvent is introduced into the distillation column simultaneously with the mixture comprising ethylbenzene and the at least one other C8 aromatic compound.

An embodiment of the present invention can further involve withdrawing an overhead stream enriched in ethylbenzene, relative to the mixture entering the distillation column, from an upper portion of the distillation column. This ethylbenzene rich stream can be directly sent to a downstream process which requires ethylbenzene as a raw material. In a more specific case, the ethylbenzene rich stream may be subjected to further treatment, such as further purification, prior to entering some downstream industrial process which requires a more purified ethylbenzene. In a preferred embodiment, at least part of the overhead stream enriched in ethylbenzene is condensed and returned to the distillation column as reflux. Concentration of ethylbenzene in the overhead stream can be widely varied according to operating conditions employed.

The process of the present invention can also further involve withdrawing a bottom stream from a lower portion of the distillation column. This bottom stream is preferably ethylbenzene lean and predominantly comprises the extractive solvent and the C8 aromatic compound heavier than ethylbenzene. It is preferred that the bottom stream is subjected to a subsequence separation unit to recover the extractive solvent and produce a C8 aromatic product from this stream. The recovered extractive solvent is then recycled to the distillation column. In a specific embodiment where the C8 aromatic compound comprises a significant portion of p-xylene when an optimized operating condition is applied, the C8 aromatic product can contain less than 20 wt % of ethylbenzene and can be further utilized as a mixed xylene isomer grade.

The present invention also relates to the use of sub-atmospheric pressure in a distillation column in a process for the distillative separation of ethylbenzene from a mixture comprising ethylbenzene and at least one other $C_8$ aromatic compound for increasing the efficiency of the separation, so that e.g. the reflux ratio can be reduced.

Embodiments of the present invention are further illustrated in the following example without limiting the invention as claimed.

EXAMPLE

Example 1

A computer simulation has been performed using the simulation software "Aspen HYSYS®", simulating that a feed stream containing 64.93 wt % ethylbenzene, 7.9 wt % p-xylene, 18.14 wt % m-xylene and 9.02 wt % o-xylene was fed at a feed rate of 15000 kg/h to an extractive distillation column having 130 stages. Various extractive solvents as shown in Table 1 were introduced into the extractive distillation column at stage 7, i.e. a location above the point of introduction of the feed stream at stage 74. As comparative examples, simulations have been run where no solvent is introduced. The operating temperatures were simulated along the column within the range of 75° C. to 175° C. The pressure in the column was simulated to be 200 mbar and 1000 mbar, respectively (see Table 1 below). The weight ratio of the solvent to the feed stream was fixed at 5:1. The simulation model further included the features that an ethylbenzene-rich stream was withdrawn at the top of the column and an ethylbenzene-lean stream was withdrawn at the bottom of the column. A portion of the ethylbenzene-rich stream from the top of the column was simulated to be returned to the column as reflux at a reflux ratio of 8.5.

It can be seen in Table 1 that a reduction of the pressure in the distillation column from 1000 mbar to 200 mbar, i.e. to sub-atmospheric pressure, the separation efficiency of the process is improved. In particular, upon reducing the pressure in the column the concentration of ethylbenzene in the overhead stream is significantly increased, even if no solvent is used.

In Table 1 below, TCB is 1,2,4-trichlorobenzene, NMP is N-methyl-2-pyrrolidone, and NFM is N-formylmorpholine.

TABLE 1

| Solvent | EB concentration in overhead wt % | EB concentration in overhead wt % |
| --- | --- | --- |
| TOP PRESSURE [mbar] | 200 | 1000 |
| NO SOLVENT | 89.04 | 84.71 |
| TCB | 99.78 | 96.22 |
| NITROBENZENE | 99.99 | 99.99 |
| BENZONITRILE | 86.85 | 84.60 |
| ISOPHORONE | 98.93 | 93.64 |

TABLE 1-continued

| Solvent | EB concentration in overhead wt % | EB concentration in overhead wt % |
|---|---|---|
| METHYL-SALICYLATE | 98.90 | 94.53 |
| BENZALDEHYDE | 94.20 | 90.85 |
| SULFOLANE | 99.99 | 99.96 |
| NMP | 99.98 | 99.84 |
| NFM | 99.99 | 99.98 |

The invention claimed is:

1. A process for the distillative separation of ethylbenzene from a mixture comprising ethylbenzene and at least one other C8 aromatic compound, the process comprising:
   adding at least one solvent to a distillation column, the at least one solvent including one or more of chloroform, carbon tetrachloride, dimethylamine, diethylamine, acetonitrile, acetaldehyde, 1-propanal, methyl isopropyl ketone, 3-methyl-2-pentanone, 3,3-dimethyl-2-butanone, 2-pentanone, 2-methylpropanal, 1-butanal, cyclopentanone, acetone, or ethanol;
   adding one or more of water or steam to the distillation column; and
   distilling said mixture in the distillation column in the presence of an extractive solvent, the at least one solvent, the one or more of water or steam, and at a sub-atmospheric pressure.

2. The process according to claim 1 wherein the extractive solvent has a boiling point above 150° C.

3. The process according to claim 1 wherein the extractive solvent comprises an organic compound selected from the group consisting of Cl-containing compounds, S-containing compounds, N-containing compounds, O-containing compounds, and mixtures thereof.

4. The process according to claim 3 wherein the extractive solvent includes at least one Cl-containing compound is selected from the group consisting of 2,4-dichlorobenzene, 1,2,3-trichlorobenzene, 1,2,4-trichlorobenzene, 1,2,4,5-tetrachlorobenzene, polychlorobenzenes, benzene hexachloride, 2,3,4,6-tetrachlorophenol, and 1,2,3-trichloropropane.

5. The process according to claim 3, wherein the extractive solvent includes at least one S-containing compound selected from the group consisting of dimethylsulfoxide, sulfolane, methyl sulfolane, and mixtures thereof.

6. The process according to claim 3, wherein the extractive solvent includes at least one N-containing compound selected from the group consisting of N-formylmorpholine, aniline, 2-pyrrolidinone, quinolone, n-methyl-2-pyrrolidone, n-methylaniline, benzonitrile, nitrobenzene, and mixtures thereof.

7. The process according to claim 3, wherein the extractive solvent includes at least one O-containing compound is selected from the group consisting of methyl salicylate, methylbenzoate, n-methyl-2-pyrrolidone, 1,2-propanediol, 1,2-butanediol, 1,3-butanediol, benzaldehyde, phenol, tetrahydrofurfuryl alcohol, diethyl maleate, ethyl acetoacetate, 4-methoxy acetophenone, isophorone, 5-methyl-2-hexanone, 2-heptanone, cyclohexanone, 2-octanone, 2-nonanone, 3-heptanone, diisobutylketone, 5-nonanone, benzyl alcohol, and mixtures thereof.

8. The process according to claim 1 wherein the sub-atmospheric pressure is in a range of 10 to 900 mbar.

9. The process according to claim 8 wherein the sub-atmospheric pressure is in the range from 50 to 600 mbar.

10. The process according to claim 1, wherein the distillation column is operated at temperature in the range of 50 to 250° C.

11. The process according to claim 1 wherein the mass ratio of the extractive solvent to the mixture comprising ethylbenzene and the at least one other $C_8$ aromatic compound is in the range of 1:1 to 10:1.

12. The process according to claim 1 wherein the at least one other $C_8$ aromatic compound comprises a compound selected from the group consisting of p-xylene, m-xylene, o-xylene, and mixtures thereof.

13. The process according to claim 1, wherein the water and/or steam is added in an amount of 0.1 to 25 wt % based on mass flow of the extractive solvent used.

14. A process for the distillative separation of ethylbenzene from a mixture comprising ethylbenzene and at least one other $C_8$ aromatic compound, the process comprising:
   adding at least one solvent to a distillation column, the at least one solvent including one or more of chloroform, carbon tetrachloride, dimethylamine, diethylamine, acetonitrile, acetaldehyde, 1-propanal, methyl isopropyl ketone, 3-methyl-2-pentanone, 3,3-dimethyl-2-butanone, 2-pentanone, 2-methylpropanal, 1-butanal, cyclopentanone, acetone, or ethanol;
   adding one or more of water or steam to the distillation column; and
   distilling said mixture in the distillation column in the presence of an extractive solvent, the at least one solvent, and the one or more of water or steam, at a sub-atmospheric pressure and a temperature in the range of 50 to 250° C.;
   wherein the extractive solvent comprises an organic compound selected from the group consisting of 2,4-dichlorobenzene, 1,2,3-trichlorobenzene, 1,2,4-trichlorobenzene, 1,2,4,5-tetrachlorobenzene, polychlorobenzenes, benzene hexachloride, 2,3,4,6-tetrachlorophenol, and 1,2,3-trichloropropane.

15. The method of claim 14, wherein the sub-atmospheric pressure is in a range of 10 to 900 mbar.

* * * * *